United States Patent
Wetzel et al.

(10) Patent No.: US 11,053,478 B2
(45) Date of Patent: Jul. 6, 2021

(54) METHOD FOR SEPARATING VIRUS-LIKE PARTICLES FROM A CELL SUSPENSION

(71) Applicant: ARTES BIOTECHNOLOGY GMBH, Langenfeld (DE)

(72) Inventors: David Wetzel, Hilden (DE); Volker Jenzelewski, Neuss (DE); Michael Piontek, Velbert (DE)

(73) Assignee: ARTES BIOTECHNOLOGY GMBH, Langenfeld (DE)

( * ) Notice: Subject to any disclaimer, the term of this patent is extended or adjusted under 35 U.S.C. 154(b) by 232 days.

(21) Appl. No.: 16/438,013

(22) Filed: Jun. 11, 2019

(65) Prior Publication Data

US 2020/0017838 A1  Jan. 16, 2020

(30) Foreign Application Priority Data

Jul. 11, 2018 (EP) .................................. 18182888

(51) Int. Cl.
  *C12N 7/00* (2006.01)
  *C07K 14/005* (2006.01)
  *C12N 1/06* (2006.01)

(52) U.S. Cl.
  CPC .............. *C12N 7/00* (2013.01); *C07K 14/005* (2013.01); *C12N 1/063* (2013.01); *C12N 2730/10023* (2013.01)

(58) Field of Classification Search
  None
  See application file for complete search history.

(56) References Cited

PUBLICATIONS

Brocke et al., "Recombinant Hepatitis B Vaccines: Disease Characterization and Vaccine Production" In Production of Recombinant Proteins, Novel Microbial and Eukaryotic Expression Systems, 2005, Wiley-VCH Verlag GmbH & Co. KGaA, Weinheim, pp. 319-359.
European Search Report and Written Opinion received for EP Patent Application No. 18182888.0, dated Oct. 17, 2018, 6 pages of Original Document Only.
Gurramkonda et al., "Purification of hepatitis B surface antigen virus-like particles from recombinant Pichia pastoris and in vivo analysis of their immunogenic properties", Journal of Chromatography B, vol. 940, 2013, pp. 104-111.

(Continued)

*Primary Examiner* — Michelle S Horning
(74) *Attorney, Agent, or Firm* — Womble Bond Dickinson (US) LLP

(57) ABSTRACT

A method for separating virus-like particles from a cell suspension of host cells. The virus-like particles having at least one envelope protein embedded in a lipid double membrane including at least a portion corresponding to a small envelope protein of a virus of the family Hepadnaviridae. The host cells are disrupted to obtain a first suspension. A supernatant containing the virus-like particles is separated from the first suspension. Then, an adsorbent is added to the supernatant and separated off. Then, the virus-like particles are desorbed from the adsorbent by adding a desorption buffer. A soluble calcium salt is added to a supernatant separated from the second suspension to form a precipitate, the precipitate formed is separated off and transferred to a third suspension. The virus-like particles are separated from the third suspension and purified.

19 Claims, 2 Drawing Sheets

(56) References Cited

PUBLICATIONS

Figure 1:
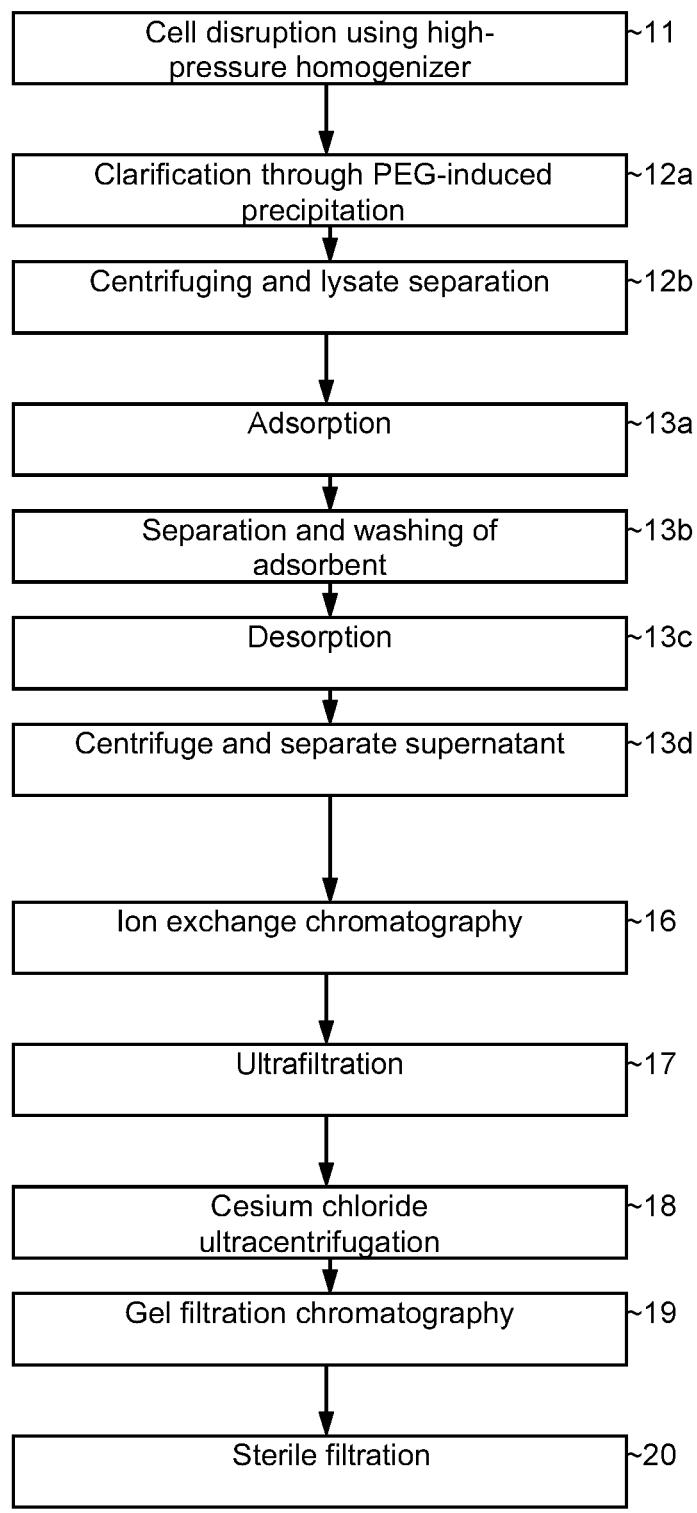

Hadiji-Abbes et al., "Extraction and purification of hepatitis B virus-like M particles from a recombinant *Saccharomyces cerevisiae* strain using alumina powder", Journal of Virological Methods, vol. 187, 2013, pp. 132-137.

Wetzel et al., "Establishment of a yeast-based VLP platform for antigen presentation", Microbial Cell Factories, vol. 17, 2018, pp. 1-17.

Zahid et al., "Assessing stability and assembly of the hepatitis B surface antigen into virus-like particles during down-stream processing", Vaccine, vol. 33, 2015, pp. 3739-3745.

Schaefer et al., "Recombinant hepatitis B Vaccines—Disease Characterization and Vaccine Production", Hansenula Polymorpha—Biology and Applications, Chapter 12, 2002, pp. 175-210.

METHOD FOR SEPARATING VIRUS-LIKE PARTICLES FROM A CELL SUSPENSION

The invention relates to a method for separating virus-like particles from a cell suspension of host cells containing the virus-like particles, wherein the virus-like particles have at least one envelope protein embedded in a lipid double membrane, comprising at least a portion corresponding to a small envelope protein of a virus of the family Hepadnaviridae, wherein
  a) the host cells are disrupted in order to obtain a first suspension containing the virus-like particles,
  b) a supernatant containing the virus-like particles is separated from the first suspension,
  c) an adsorbent is added to the supernatant separated from the first suspension such that the virus-like particles are adsorbed by the adsorbent,
  d) the adsorbent with the adsorbed virus-like particles is separated off,
  e) the virus-like particles are desorbed from the separated-off adsorbent, so that they pass into a supernatant of a second suspension formed thereby, and
  f) the supernatant containing the virus-like particles is separated from the second suspension,
wherein subsequently the virus-like particles are separated from the separated-off supernatant and purified.

Such a method is known, for example, from S. Schaefer, M. Piontek, S.-J. Ahn, A. Papendieck, Z. A. Janowicz, I. Timmermans and G. Gelissen: "Recombinant hepatitis B vaccines—disease characterization and vaccine production", chapter 12.3.3, in G. Gellissen (ed): "*Hansenula polymorpha*—Biology and Applications", 2002, Wiley-VCH Verlag GmbH, Weinheim. In the process downstream of the fermentation (downstream process) described there, the host cells of the yeast species *Ogataea angusta* (*Hansenula polymorpha*), which contain virus-like particles, are first harvested, the virus-like particles having envelope proteins HBsAg (hepatitis B surface antigen) embedded in a lipid double membrane. A cell disruption process follows by means of grinding in a glass ball mill or by high-pressure homogenization. As a result, there is a first suspension containing only a few intact host cells and the components of the destroyed host cells, including the released virus-like particles. This is followed by centrifugation, in which a supernatant is separated off and fed to further processing. The supernatant contains the virus-like particles which are specifically bound to a suitable adsorbent in a subsequent adsorption step. The adsorbent is chosen so that the major part of the virus-like particles is bound thereto, while most of the remaining proteins of the host cells remain in the supernatant. The unbound proteins in the supernatant are removed by washing the adsorbent with the virus-like particles attached thereto. The washed adsorbent is then resuspended with a desorbent, with the majority of the virus-like particles dissolving from the adsorbent. The supernatant containing the virus-like particles is separated off and fed to further purification steps. The further purification steps include ion exchange chromatography and ultrafiltration followed by cesium chloride density gradient centrifugation. This ultracentrifugation is followed by gel filtration chromatography to remove the cesium salt from the product.

Disadvantages of the known process are the relatively high costs that arise, in particular, from the step of cesium chloride density gradient centrifugation with subsequent gel filtration chromatography.

It is therefore an object underlying the invention to provide a method in which, with comparable purity of the virus-like particles a subsequent cesium chloride density gradient centrifugation can be dispensed with.

This object is achieved by a method having the features of claim 1. That is, in a method of the type mentioned above, this object is achieved in that in step e) for desorbing the virus-like particles a desorption buffer is added which contains deoxycholic acid and/or at least one soluble salt of deoxycholic acid, and that after step f):
  g) a soluble calcium salt is added to the separated-off supernatant, forming a precipitate containing a calcium salt of the deoxycholic acid and the virus-like particles,
  h) the precipitate formed is separated off and transferred to a third suspension and
  i) the virus-like particles are separated from the third suspension and purified.

In the method according to the invention for separating virus-like particles from a cell suspension of host cells containing the virus-like particles, the host cells are first disrupted in a step a) in order to obtain a first suspension containing the virus-like particles. The disruption of the host cells can be carried out by any suitable method, such as those also mentioned in the above-mentioned prior art. The first suspension thus contains all constituents of the host cells, including the released virus-like particles, which have at least one envelope protein embedded in a lipid double membrane which comprises at least one segment which corresponds to a small envelope protein of a virus of the Hepadnaviridae family. The small envelope protein is the smallest of several envelope proteins formed by these viruses. When referring to the fact that the virus-like particles have "at least one" envelope protein, this refers to the nature of the envelope proteins and regularly means that a large number of molecules of this envelope protein are embedded in the lipid double membrane of the particles. Usually, a plurality of envelope protein molecules, for example about 100 envelope protein molecules, are embedded in the lipid double membrane of the virus-like particle. In addition, this does not exclude that several different envelope proteins may be embedded in the lipid double membrane. In addition, when it is said that the envelope protein comprises "at least one portion" corresponding to a small envelope protein of a virus of the family Hepadnaviridae, this means in the simplest case that the envelope protein consists of the small envelope protein of a virus of the family Hepadnaviridae. However, it generally means that the envelope protein, in addition to the small portion corresponding to the envelope protein comprises further portions which either correspond to the other portions of other envelope proteins of the same virus of the family Hepadnaviridae or correspond to the protein portions of other organisms. In addition, several different portions can be coupled to the at least one portion corresponding to the small envelope protein. The composition of the lipid double membrane corresponds to that of the lipid double membranes of the host cell.

In a second step b), a supernatant containing the virus-like particles is separated from the first suspension. For example, this separation off is carried out by the centrifugation customary here, wherein the supernatant formed, the lysate, is supplied for further processing.

Subsequently, in a third step c), an adsorbent is added to the separated supernatant so that the virus-like particles are adsorbed by the adsorbent. For example, a lysate in a buffer solution is mixed with a suitable adsorbent, wherein the buffer solution has a pH value suitable for adsorption of the virus-like particles to the adsorbent. As adsorbent, for example, pyrogenic or precipitated silica or glass milk or other substance having a hydrophilic surface having silanol groups (—Si—OH) can be used. At this step, adsorption of the virus-like particles to the adsorbent takes place. This adsorption usually requires a certain time, so that, for example, the mixture of the lysate and the adsorbent is stirred for a certain period of time under given reaction conditions.

Subsequently, in step d), the adsorbent with the adsorbed virus-like particles is separated off. For example, the suspension containing the adsorbent is centrifuged, the resulting precipitate, the so-called "pellet", is resuspended in a wash solution, the resulting wash solution suspension is then centrifuged and the resulting precipitate ("pellet") containing the washed adsorbent particles with adsorbed virus-like particles, is separated off.

In a subsequent step e), the virus-like particles are desorbed from the separated-off adsorbent, so that they pass into a supernatant of a second suspension formed thereby. This is done, for example, by resuspending ("dissolving") a precipitate or pellet of the separated-off washed adsorbent (with adsorbed virus-like particles) with the addition of a desorbent in a buffer solution, the buffer solution providing an appropriate pH level for a desorption of the virus-like particles from the adsorbent. To desorb the virus-like particles—in a conventional manner—a desorption buffer is added, which contains as detergent deoxycholic acid and/or at least one soluble salt of deoxycholic acid. In addition, the desorption buffer may contain conventional buffering ingredients such as borates and EDTA (ethylenediaminetetraacetic acid).

Subsequently, in a step f), the supernatant of the second suspension, which now contains the virus-like particles, is separated from the second suspension, for example by centrifuging. In the following steps, the virus-like particles are separated from the separated-off supernatant and purified.

In particular, in a step g) a soluble calcium salt is added to the separated-off supernatant, wherein a precipitate is formed, which contains a calcium salt of the deoxycholic acid and the virus-like particles. At this step, deoxycholic acid is precipitated by addition of divalent cations, specifically calcium ions. Surprisingly, it has been found here that the addition of the soluble calcium salt, for example of calcium chloride, together with the deoxycholic acid also causes the predominant part of the virus-like particles to enter the precipitate, that is to say co-precipitate.

The precipitate thus formed, which contains the virus-like particles, is separated off in a step h) and transferred to a third suspension. For example, the precipitate is separated off by centrifugation and the resulting "pellet" is resuspended in a buffer solution. The pH value of the buffer solution is adjusted so that the deoxycholic acid dissolves, preferably to a slightly alkaline value of e.g. 8.5. The buffer solution used here contains, for example, a pH stabilizer such as TRIS (tris (hydroxymethyl) aminomethane), a chelator such as EDTA, and a salt such as NaCl to increase ionic strength.

Subsequently, in step i) the virus-like particles are separated from the third suspension and purified. This final separation and purification of the virus-like particles can be carried out, for example, as in the abovementioned known method, by means of a chromatographic method and a filtration.

The decisive advantage of the method according to the invention is that due to the purity of the third suspension, which is essentially based on the intermediate precipitation step g), the subsequent expensive steps of cesium chloride density gradient centrifugation and size exclusion chromatography can be dispensed with.

A preferred embodiment of the method is characterized in that in step e) a desorption buffer is added, which contains the deoxycholic acid or the soluble salt of deoxycholic acid in a molar concentration between 1 mmol/l and 10 mmol/l, preferably in a molar concentration of about 6 mmol/l. This concentration of the detergent or surfactant deoxycholic acid known in the prior art for this desorption step as such ensures sufficient desorption of the virus-like particles.

In this case, preferably in step g), the soluble calcium salt in a molar concentration between 30 mmol/l and 100 mmol/l, preferably between 40 mmol/l and 60 mmol/l, is added to the separated supernatant. It showed an optimal concentration at about 50 mmol/l; at lower concentrations, the proportion of precipitated virus-like particles decreased and higher concentrations did not result in a substantial increase in the precipitated portion, but are less economical. In order to achieve a precipitation of the deoxycholic acid on addition of the calcium salt, a suitable pH value in the acidic range is set. Preferably, a pH value between 4 and 5.5 is set here. In this case, a temperature of 4-8° C. is preferably set, wherein the duration of the precipitation step is for example about 6 hours.

Preferably, in step e) for desorbing the virus-like particles from the adsorbent, the desorption buffer containing the deoxycholic acid and/or the soluble salt of deoxycholic acid is added in an amount 0.1 to 4 times the volume of the supernatant separated from the first suspension containing the disrupted host cells in step b). For example, the desorption buffer is added in an amount corresponding to 0.25 times, i.e. a quarter, of the volume of the supernatant which has been separated from the first suspension in step b). Preferably, two desorption steps are connected in series, wherein in each case the desorption buffer is added in an amount corresponding, for example, to 0.125 (one-eighth) of the volume of the supernatant separated from the first suspension in step b). In this case, a first portion of the desorption buffer is first added to the adsorbent separated off in step d), then the supernatant is separated off and stored, then a second portion of the desorption buffer is added to the separated-off adsorbent and the supernatant is separated off again. Finally, the two quantities of each separated-off supernatant are combined. The amount of desorption buffer used and the second washing step increase the yield.

In step g), soluble calcium salts may be used, such as calcium chloride, calcium ascorbate, calcium lactate, calcium gluconate, calcium lactate gluconate or calcium nitrate. Preferably, calcium chloride is added to the separated supernatant in step g).

In a preferred embodiment, a nonionic surfactant is added to the separated-off supernatant in step c) such that (during adsorption) a concentration of the nonionic surfactant between 0.006 g/ml and 0.01 g/ml, preferably a concentration of about 0.008 g/ml, is set. Preferably, as non-ionic surfactant, polysorbate 20 (Tween® 20; "Tween" is a registered trademark of Croda Americas LLC) is admixed with the separated-off supernatant. This detergent polysorbate 20 is preferably already in cell disruption in step a) in the first suspension. The addition in step c) serves in this case to increase the concentration of polysorbate 20. Surprisingly, the addition of the nonionic surfactant polysorbate 20 had an effect on the binding of host proteins and virus-like particles to the surface of the fumed silica used as adsorbent; the proportion of adsorbed host proteins could be lowered. In this way, an increase in purity was achieved. Setting a concentration of about 0.008 g/ml is preferred; a further increase in concentration, especially beyond 0.01 g/ml, did not result in any significant improvement.

In an advantageous further development of the method for separating virus-like particles from a cell suspension, in step d) the adsorbent with the adsorbed virus-like particles is separated off by washing the adsorbent with the adsorbed virus-like particle, whereby urea is added to the wash solution. Surprisingly, the addition of urea to the wash solution had an effect on the purity of the product, although no effects of urea addition on adsorption could be detected. Basically, the addition of urea to the wash solution increases the proportion of washed off host proteins and the proportion of washed-off virus-like particles, but disproportionately the proportion of washed-off host proteins.

Preferably, in this case, the adsorbent with the adsorbed virus-like particles is washed by adding urea in a first washing step to the wash solution in a molar concentration between 2 mol/l and 6 mol/l, preferably in a molar concentration of about 4 mol/l, and in a second washing step with an aqueous sodium chloride solution. As already mentioned, the addition of urea to the wash solution increases the proportion of washed-off host proteins and the proportion of washed-off virus-like particles, but disproportionately increases the proportion of washed-off host proteins. At a urea molar concentration between 2 mol/l and 6 mol/l, preferably of about 4 mol/l, this disproportionate share is particularly high. The second washing step serves to reduce the urea carry-over in the desorption mixture.

In one embodiment of the invention in step h), the precipitate formed is converted into a third suspension by the precipitate being dissolved in a weakly basic buffer solution. The pH value is chosen so that the deoxycholic acid of the precipitate goes into solution. The virus-like particles contained in the precipitate also enter the third suspension, which due to its clarity is herein also referred to as "solution". The pH value is preferably adjusted to a slightly alkaline value of about 8.5. The buffer solution used here includes, for example, a pH stabilizer such as TRIS hydrochloride (tris (hydroxymethyl) aminomethane hydrochloride), a chelator such as EDTA, and a salt such as NaCl to increase ionic strength.

In a preferred embodiment of the method for separating virus-like particles from a cell suspension, the virus-like particles are separated off in step i) using a chromatographic method. Preferably, the chromatographic method is preceded by a filtration to remove particles which could clog the chromatography matrix (for example, 0.45 µm filtration). Further, in a preferred embodiment, this chromatography step is followed by combined diafiltration for desalting and buffer exchange, and ultrafiltration for concentration.

In a preferred embodiment of the method, an anion exchange chromatography is carried out as a chromatographic method, wherein a surfactant is added to the eluent. This serves, in particular, to remove the deoxycholic acid initially precipitated in step g) but then remaining in the suspension by re-dissolution in step h). In this case, polysorbate 20 (Tween® 20) is preferably added to the eluent as surfactant in step j). This increases the yield.

In an alternative embodiment of the method, a multimodal chromatography is performed as the chromatographic method in place of the anion-exchange chromatography. In contrast to the anion-exchange chromatography, the virus-like particles are not bound here, which accelerates the process. Since it does not have to be eluted, there is also a saving of material.

In one embodiment of the method for separating virus-like particles from a cell suspension of host cells containing the virus-like particles, the virus-like particles have an envelope protein embedded in the lipid double membrane, comprising at least a portion which corresponds to the small envelope protein (s-HBsAg) of a human hepatitis B virus.

In a preferred embodiment of the method of separating virus-like particles from a cell suspension of host cells containing the virus-like particles, the virus-like particles comprise an envelope protein embedded in the lipid double membrane and comprising at least a portion corresponding to the small envelope protein (s-dHBsAg) of a duck Hepatitis B virus.

Preferably, the virus-like particles comprise an envelope protein which is a hybrid protein having a portion corresponding to the small envelope protein of a virus of the Hepadnaviridae family and at least one target epitope-forming portion. This allows the creation of virus-like particles with selectable epitopes that are part of a desired antigen.

In a further development of this embodiment, the hybrid protein has at least two portions each forming a target epitope. This simplifies the creation of virus-like particles that present different epitopes of different antigens on their surface.

In the embodiments wherein the envelope protein is a hybrid protein having a portion corresponding to the small envelope protein of a virus of the Hepadnaviridae family and at least one portion forming a target epitope, the at least one target epitope preferably corresponds to an epitope of a virus of a group comprising bovine viral diarrhea viruses, West Nile viruses and swine fever viruses. This enables the cost-effective production of vaccines based on virus-like particles.

In the method according to the invention for separating virus-like particles from a cell suspension of host cells containing virus-like particles, it is preferred that the host cells are cells of a recombinant yeast strain of the order Saccharomycetales (genuine yeasts) or the genus *Schizosaccharomyces* (fission yeasts). Preferably, the host cells are cells of a recombinant strain of *Ogataea angusta* (*Hansenula polymorpha*). These yeast host organisms combine the advantages of simple genetic manipulation and eukaryotic post-translational modification with high productivity and a cost-effective fermentation process.

Advantageous and/or presently preferred embodiments of the invention are characterized in the subclaims.

Figure 2:
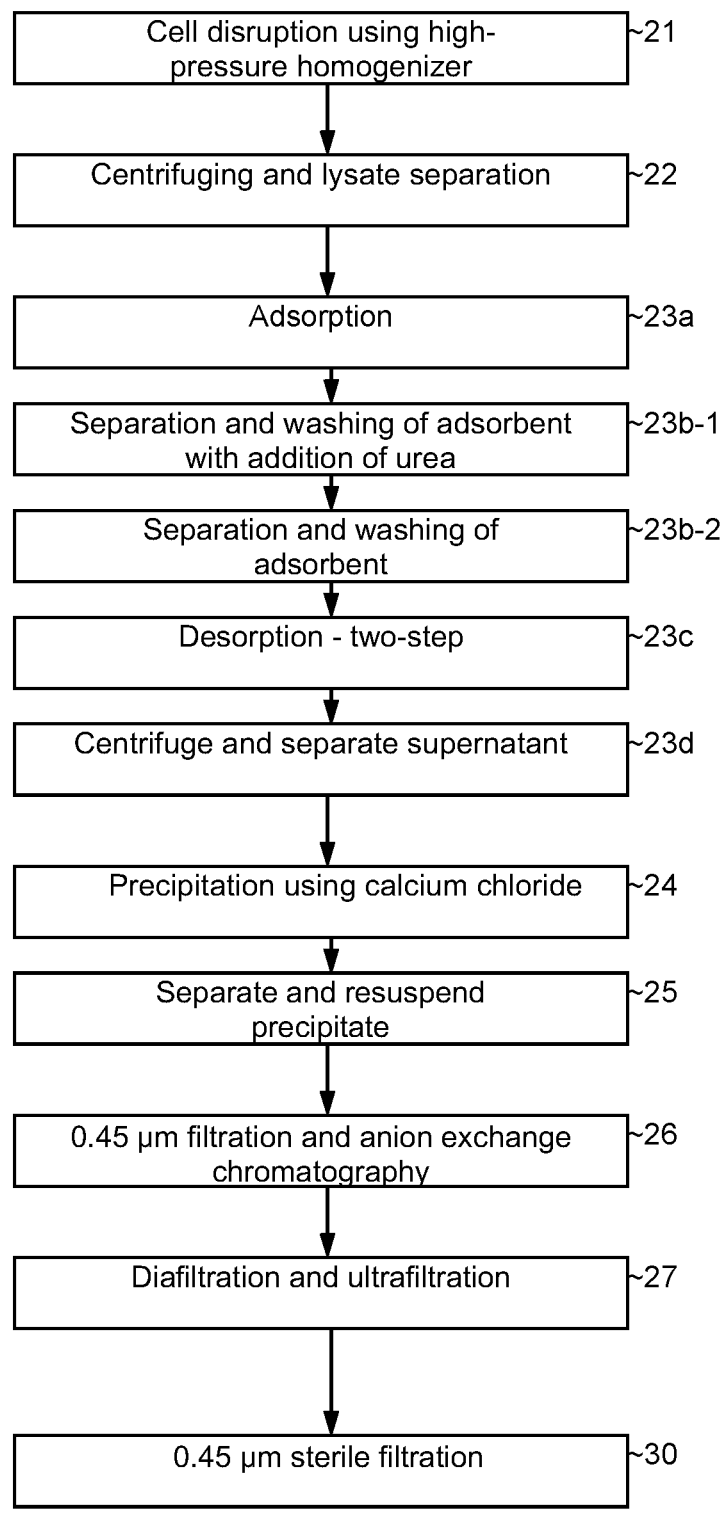

The invention will be described in detail below with reference to preferred embodiments of the method according to the invention illustrated in the drawings. The drawings show:

FIG. 1 is a schematic representation of a known method for separating virus-like particles from a cell suspension of host cells and FIG. 2 is a schematic representation of a first embodiment of the method according to the invention for separating virus-like particles from a cell suspension of host cells.

The known method illustrated in FIG. 1 for separating virus-like particles from a cell suspension of host cells is part of a downstream process known from an article by Schaefer et al. mentioned in the aforementioned article: "Recombinant hepatitis B vaccines—disease characterization and vaccine production", chapter 12.3.3, in G. Gellissen (ed): "*Hansenula polymorpha*—Biology and Applications", 2002, Wiley-VCH Verlag GmbH, Weinheim. The downstream process begins with a harvest of yeast cells of the yeast species *Ogataea angusta* (*Hansenula polymorpha*) containing virus-like particles, the virus-like particles having envelope proteins HBsAg (hepatitis B surface antigen)

embedded in a lipid double membrane. The culture medium is replaced by a buffer which is suitable for a subsequent cell disruption. This is followed by separation of the virus-like particles from a cell suspension of harvested host cells and purification of the virus-like particles.

In the known method, the cells are first disrupted by high-pressure homogenization (step 11). As a result, there is a first suspension containing only a few intact host cells and the components of the destroyed host cells, including the released virus-like particles. The first suspension comprises a buffer system containing inter alia an inhibitor of intracellular proteases and detergents. This is followed by clarification of the suspension by precipitation by addition of polyethylene glycol (PEG) (step 12a) and a high-speed centrifugation (step 12b), wherein the supernatant is separated off and fed to further processing. The supernatant contains the virus-like particles which are specifically bound in a subsequent adsorption step to a suitable adsorbent (also referred to as matrix) (step 13a). The adsorbent is chosen so that the major part of the virus-like particles is bound thereto, while most of the remaining proteins of the host cells remain in the supernatant. The unbound proteins in the supernatant are removed by washing the adsorbent with the virus-like particles bound thereto (step 13b). The washed adsorbent is then resuspended with a desorbent, with the majority of the virus-like particles being released from the adsorbent (step 13c). The supernatant containing the virus-like particles is separated by centrifugation (step 13d) and fed to further purification steps. The further purification steps include ion exchange chromatography (step 16) and ultrafiltration (step 17) followed by cesium chloride density gradient ultracentrifugation (step 18) to separate residual contaminants from components of the host cells. This ultracentrifugation is followed by gel filtration chromatography (step 19) to remove the cesium salt from the product. According to the publication (Table 12.5), in this downstream process for the virus-like particles HBsAg in host cells of the yeast *Ogataea angusta* (*Hansenula polymorpha*) a purity of more than 95% (after SDS/PAGE) was achieved, the residual cesium content of less than 10 µg per 20 µg of protein remaining in the product.

In a modification of the method known from the prior art, virus-like particles were produced with the aid of a recombinant yeast strain, which particles have envelope protein molecules embedded in a lipid double membrane and comprise a first portion which corresponds to the small envelope protein of the duck hepatitis B virus (dHBsAg), and a second portion which presents an antigen derived from the glycoprotein E2 of bovine viral diarrhea virus (BVDV—bovine viral diarrhea virus). The recombinant yeast strain thus expresses a fusion protein which has the particle-forming envelope protein dHBsAg at its C-terminus and the BVDV E2 protein at its N-terminus (gene bank accession number: AEV54362.1). First, the virus-like particles were separated off and purified by a method which substantially corresponds to the above-mentioned known method. This is for comparison with the method of the invention described below.

After harvesting the host cells containing the virus-like particles, six cycles of high pressure homogenization were performed at 65±1 g DCW/l in a cell disruption buffer (25 mmol/l sodium phosphate, 2 mmol/l EDTA, pH=7.9) containing 0.07 g polysorbate 20 per 1 g DCW (equivalent to 0.46% (w/v) Polysorbate 20) and 2 mmol/l of the protease inhibitor phenylmethylsulfonyl fluoride (PMSF). The lysate was directly centrifuged (17,000 g, 4° C., 30 min) and the supernatant ("APV-SN") was processed further. The clarification of the lysate by the addition of $PEG_{6000}$ and NaCl known from the above prior art was omitted. Fumed silica (Aerosil 380 V, Evonik) was added to the supernatant as an adsorbent (15 g/l), and the mixture was left overnight at 4° C. on a magnetic stirrer for adsorption. The adsorbent (with adsorbed particles) was then separated off and washed with saline solution (77 mmol/l), the volume of the wash solution being volume normalized to the volume of supernatant APN-SN. Subsequently, the product was desorbed by adding a desorption buffer (10 mmol/l disodium tetraborate decahydrate, 2 mmol/1 EDTA and 6 mmol/l sodium deoxycholate (DOC), pH=9.1) using one quarter of the volume of supernatant APV-SN (stirred for one hour at 25° C.). The suspension was then centrifuged (17,000 g, 18° C., 30 min), after which the supernatant (desorbate) was filtered (0.45 μm) to remove silica particles. A 50 mmol/l TRIS hydrochloride buffer (pH=8.5, ~8 mS/cm) was then added to the filtered desorbate and anion exchange chromatography performed. The product was diluted with 0.5 mol/l NaCl in 50 mmol/l TRIS hydrochloride buffer (pH=8.5) and desalted by diafiltration followed by concentration by ultrafiltration. The retentate was subjected to density gradient ultracentrifugation (1.5 mol/l cesium chloride, 65 hrs. at 48,400 rpm, 4° C.). This ultracentrifugation was followed by size exclusion chromatography to remove the cesium salt from the product. Finally, sterile filtration (0.45 μm) followed.

This separation and purification process, which is similar to the conventional process, as expected, produced results that were consistent with the known process. This shows that the purification procedures for the HBsAg particles and the E2-BVDB-dHBsAg particles are comparable. As expected, the results of the purification process according to the invention described below can be transferred to a group of virus-like particles which have at least one envelope protein embedded in a lipid double membrane which comprises at least one portion which corresponds to a small envelope protein of a virus of the Hepadnaviridae family. In the purification process according to the known method, after the adsorption/desorption steps (corresponding to steps 13*a*-13*d* of FIG. 1) the purity was 20%, after the steps of ion exchange chromatography and ultrafiltration (steps 16 and 17 of the prior art method according to FIG. 1) the purity was 29%, after the steps of ultracentrifugation with subsequent gel filtration chromatography (steps 18 and 19 of the known method) the purity was 90%, and after the final 0.45 μm sterile filtration the purity still was 90%. From these results it can be seen that cesium chloride ultracentrifugation makes a significant contribution to achieving the desired purity, so that abandoning this step to reduce costs does not appear to be performable or at least not without substantial modification of the other purification steps.

FIG. 2 shows the schematic sequence of a preferred exemplary embodiment of the method according to the invention for separating virus-like particles from a cell suspension. Cell disruption by high pressure homogenizer (step 21) and the step of centrifugation and lysate separation (step 22) are performed as in the previously described procedure.

The adsorption/desorption steps (steps 23*a*-23*d*) are modified as follows. First, various conditions were tested to increase the purity during adsorption. Surprisingly, it was found that the addition of the non-ionic detergent polysorbate 20 (Tween® 20) had effects on the binding of host proteins and the virus-like particles to the ionic surface (silanol groups) of the fumed silica (Aerosil). It was considered that this detergent is already in the cell disruption in the sample (cell disruption buffer). In various tests, the concentration was gradually increased from 0.004 g/ml (no additional polysorbate 20) up to 0.014 g/ml. At concentrations up to about 0.008 g/ml, there was a reduction in the proportion of host proteins bound to the fumed silica compared to the bound virus-like particles. A further increase from about 0.01 g/30 ml showed no further improvements. Therefore, in the preferred embodiment of the method according to the invention, a proportion of 0.008 g/ml polysorbate 20 in the adsorption buffer is selected.

The known step of washing with saline (step 23b-2) is preceded by a further washing step (step 23b-1). First, various additives to the wash solution were tested for increasing the purity of the product. Surprisingly, the addition of urea to the wash solution had an effect on the purity of the product, although this substance previously had no effect in optimizing adsorption. Urea concentrations of up to 8 mol/l were tested. The higher the urea concentration was chosen, the more host proteins but also virus-like particles were washed off by the fumed silica. At about 4 mol/l urea, the proportion of washed-off host proteins was disproportionately high compared to the proportion of washed-off virus-like particles. Therefore, in the preferred embodiment of the method according to the invention a proportion of 4 mol/l urea in a 50 mmol/l sodium phosphate buffer (pH=7.0) is selected. In the second washing step, as in the known washing step, an aqueous 77 mmol/l NaCl solution is selected. Each washing step is preceded by separation off of the adsorbent by centrifugation, after which the separated adsorbent is resuspended in the respective wash solution. The second washing step is again followed by a separation of the washed adsorbent by centrifugation.

The subsequent step of desorption (step 23c) is also modified in comparison with the known desorption step (step 13c according to FIG. 1). A desorption buffer is added to the washed adsorbent separated by centrifugation. It was found that at a higher volume of the desorption buffer, the product yield increases. Therefore, the volume of the desorption buffer was increased and a second desorption step was introduced. While in the aforementioned process, which corresponds to the conventional method, a desorption buffer was added in a volume which corresponds to a quarter of the volume of the supernatant APV-SN, in the modified desorption step a first portion of the desorption buffer is added to the separated-off adsorbent in a volume corresponding to one-eighth of the volume of the supernatant APV-SN, then the supernatant was separated off and stored, then a second portion of the desorption buffer added to the separated-off adsorbent, which in turn corresponded to one-eighth of the volume of the supernatant APV-SN, and again the supernatant was separated off. Finally, the two quantities of each separated-off supernatant are combined. Incidentally, in the preferred embodiment of the process of the present invention, the desorption buffer used corresponds to the desorption buffer described above, which is used in the process according to the conventional method.

The supernatant obtained for further processing after the desorption step contains, in addition to the virus-like particles to be separated off and undesired constituents of the host cells (in particular host proteins), also the deoxycholic acid ions of the desorption buffer. According to the invention, these are precipitated by the addition of divalent cations, for example calcium ions. This is preferably carried out in the acidic range at a pH value between 4 and 5.5. Since it is an object of the improvement of the purification process according to the invention to keep the costs low, calcium ions are used as divalent cations. Surprisingly, it has been found that addition of the calcium ions not only precipitates the deoxycholic acid (DOC), but at the same time also precipitates the virus-like particles. Both the DOC and the virus-like particles pass into a precipitate (also referred to as a pellet), while a large part of the undesirable components of the host cells remain in the supernatant. The calcium ions are preferably supplied in the form of calcium chloride, wherein, for example, using a 1 mol/l-$CaCl_2$ solution, a concentration of 50 mmol/l is set in the desorption buffer. The desorption buffer, for example, acts at a temperature between 4 and 8° C. for a period of about six hours.

Subsequently, the suspension is centrifuged (17,000 g, 30 min, 18° C.) and the pellet thus obtained dissolved again, wherein the virus-like particles contained therein are transferred into a suspension (step 25 according to FIG. 2). The pellets are dissolved in a weakly alkaline buffer, with a pH value between 7.5 and 8.5 improving the solubility of the deoxycholic acid. The buffer used contains, for example, 15 mmol/l TRIS hydrochloride as a pH stabilizer, 100 mmol/l sodium chloride to increase the ionic strength and 20 mmol/l EDTA as a chelator. Preferably, a pH value of 8.5 is set. EGTA was tested instead of EDTA, with EDTA giving better results than EGTA, although EGTA is described in the literature as a better complexing agent for $Ca^{2+}$ ions.

In a subsequent step (step 26), the suspension thus prepared is filtered at 0.45 μm and then fed to anion exchange chromatography. The filtering is used to remove particles that can clog the subsequent chromatography. The anion exchange chromatography (AIEC) is required in particular for the removal of deoxycholic acid remaining in the sample. In this case, in the preferred method, for example, an elution buffer is used which contains 500 mmol/l NaCl and 0.1% by volume of polysorbate 20 in 50 mmol/l TRIS hydrochloride buffer (pH=8.5). The addition of the nonionic surfactant polysorbate 20 increases the yield.

In an alternative embodiment of the method of the invention, anion exchange chromatography in step 26 could be replaced by multimodal chromatography that combines the principles of different types of chromatography, such as gel filtration with ion exchange chromatography and hydrophobic interaction chromatography. Multimodal chromatography uses a different principle compared to anion exchange chromatography: The virus-like particles are not bound to the chromatography matrix. Only the, compared to the virus-like particles, relatively small contaminants (e.g., host cell proteins) penetrate the beads of the matrix of multimodal chromatography and either bind to the ligands or are separated from the virus-like particles by diffusion-related time delay when flowing through the column flows. As a result, depending on the nature of the contaminating host cell proteins, there may be an advantage over the anion exchange chromatography with regard to the purity of the virus-like particles. In addition, this procedure is faster because the virus-like particles are not bound and therefore need not be eluted, which also results in a savings potential for the materials, because in the elution step of anion exchange chromatography, a significant amount of NaCl must be used (500 mmol/l to 1 mol/l). Chromatography of step 26 is followed by diafiltration and ultrafiltration as already used in the abovementioned known process, which is the conventional method. Finally, a 0.45 μm sterile filtration is performed.

In the method according to the invention a purity of the virus-like particles of 72% showed in the experiments carried out already after the step of precipitation by means of calcium chloride and the re-dissolution of the thus built pellet. This corresponds approximately to the purity achieved in the conventional method after ultracentrifugation. Due to this surprising result, the expensive step of cesium chloride ultracentrifugation with subsequent gel filtration chromatography can be dispensed with. In the experiments carried out, the purity after the ultrafiltration (step 27) and after the final sterile filtration was 84%. In the alternative method using multimodal chromatography instead of anion exchange chromatography, the purity after ultrafiltration (step 27) was 83%. After the final 0.45 μm filtration, a purity of 94% was noted. However, a significant loss of the product was observed in the final filtration, which could be due to increased formation of clusters or aggregates of the virus-like particles. The multimodal octylamine ligands used may possibly remove components, such as lipids, which are essential for the formation of the virus-like particles.

The invention claimed is:

1. A method for separating virus-like particles from a cell suspension of host cells containing the virus-like particles, wherein the virus-like particles have at least one envelope protein embedded in a lipid double membrane, the protein comprising at least a portion corresponding to a small envelope protein of a virus of the family Hepadnaviridae, wherein
   a) the host cells are disrupted in order to obtain a first suspension containing the virus-like particles,
   b) a supernatant containing the virus-like particles is separated from the first suspension,
   c) an adsorbent is added to the supernatant separated from the first suspension such that the virus-like particles are adsorbed by the adsorbent,
   d) the adsorbent with the adsorbed virus-like particles is separated off,
   e) the virus-like particles are desorbed from the separated-off adsorbent, so that they pass into a supernatant of a second suspension formed thereby, and
   f) the supernatant containing the virus-like particles is separated from the second suspension,
   wherein subsequently the virus-like particles are separated from the separated-off supernatant and purified,
   wherein in step e) for desorbing the virus-like particles a desorption buffer is added which contains deoxycholic acid and/or at least one soluble salt of deoxycholic acid and
   wherein after step f):
   g) a soluble calcium salt is added to the separated-off supernatant, forming a precipitate containing a calcium salt of deoxycholic acid and the virus-like particles,
   h) the precipitate formed is separated off and transferred to a third suspension and
   i) the virus-like particles are separated from the third suspension and purified.

2. The method according to claim 1, wherein in step e) for desorbing the virus-like particles, a desorption buffer is added, which contains the deoxycholic acid and/or the soluble salt of deoxycholic acid, respectively, in a molar concentration between 1 mmol/l and 10 mmol/l, preferably about 6 mmol/l.

3. The method according to claim 2, wherein in step g) the soluble calcium salt is added to the separated-off supernatant in a molar concentration between 30 mmol/l and 100 mmol/l, preferably between 40 mmol/l and 60 mmol/l.

4. The method according to claim 2, wherein in step e) for desorbing the virus-like particles from the adsorbent, the desorption buffer containing the deoxycholic acid and/or the soluble salt of deoxycholic acid, respectively, is added in an amount of 0.1 times to 4 times the volume of the supernatant separated off in step b).

5. The method according to claim 1, wherein calcium chloride is added to the separated-off supernatant in step g).

6. The method according to claim 1, wherein in step c) a nonionic surfactant is added to the separated-off supernatant, so that a concentration of the nonionic surfactant between 0.006 g/ml and 0.01 g/ml, preferably from about 0.008 g/ml, is adjusted.

7. The method according to claim 1, wherein in step d) the adsorbent with the adsorbed virus-like particles is separated off, wherein the adsorbent with the adsorbed virus-like particles is washed, wherein urea is added to the wash solution.

8. The method according to claim 7, wherein the adsorbent with the adsorbed virus-like particles is washed by adding urea in a first washing step to the wash solution in a molar concentration between 2 mol/l and 6 mol/l, preferably about 4 mol/l, and washing in a second washing step with an aqueous sodium chloride solution.

9. The method according to claim 1, wherein in step h) the precipitate formed is transferred to a third suspension by dissolving the precipitate in a weakly basic buffer solution having a pH value between 7.5 and 8.5.

10. The method according to claim 1, wherein in step i) the virus-like particles are separated from the third suspension by means of a chromatographic method.

11. The method according to claim 10, wherein an anion exchange chromatography is carried out as a chromatographic method, wherein a surfactant is added to the eluent.

12. The method according to claim 11, wherein in step j) polysorbate 20 is added to the eluent as a surfactant.

13. The method according to claim 10, wherein as a chromatographic method, a multimodal chromatography is performed.

14. The method according to claim 1, wherein the virus-like particles have an envelope protein comprising at least a portion which corresponds to the small envelope protein (s-dHBsAg) of a duck hepatitis B virus or the small envelope protein (s-HBsAg) of a human hepatitis B virus.

15. The method according to claim 1, wherein the virus-like particles have an envelope protein, which is a hybrid protein with a portion corresponding to the small envelope protein of a virus of the family Hepadnaviridae and at least one portion forming a target epitope.

16. The method according to claim 15, wherein the hybrid protein has at least two portions, each forming a target epitope.

17. The method according to claim 15, wherein the at least one target epitope corresponds to an epitope of a virus of a group comprising bovine viral diarrhea viruses, West Nile viruses and swine fever viruses.

18. The method according to claim 1, wherein the host cells are cells of a recombinant yeast strain of the order Saccharomycetales (real yeasts) or the genus *Schizosaccharomyces* (fission yeasts).

19. The method according to claim 18, wherein the host cells are cells of a recombinant strain of *Ogataea angusta* (*Hansenula polymorpha*).

* * * * *